United States Patent
Eek et al.

(10) Patent No.: US 6,288,284 B1
(45) Date of Patent: Sep. 11, 2001

(54) METHOD FOR PRODUCING BIS(4-HYDROXYARYL)ALKANES

(75) Inventors: Rob Eek, Bergen op Zoom (NL); Kaspar Hallenberger, Leverkusen (DE); Christine Mendoza-Frohn, Erkrath (DE); Georg Ronge, Düsseldorf (DE); Gerhard Fennhoff, Willich (DE); Domien Sluyts, Stabroek (DE); Werner Verhoeven, Kalmthout (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/581,441

(22) PCT Filed: Dec. 8, 1998

(86) PCT No.: PCT/EP98/07973

§ 371 Date: Jul. 3, 2000

§ 102(e) Date: Jul. 3, 2000

(87) PCT Pub. No.: WO99/32423

PCT Pub. Date: Jul. 1, 1999

(30) Foreign Application Priority Data

Dec. 19, 1999 (DE) .............................................. 197 56 771

(51) Int. Cl.$^7$ ...................................................... C07C 39/16
(52) U.S. Cl. .......................................... 568/728; 568/727
(58) Field of Search ...................................... 568/727, 728

(56) References Cited

U.S. PATENT DOCUMENTS

| 3,634,341 | 1/1972 | Gammill et al. ................... 260/2.2 R |
| 3,760,006 | 9/1973 | Gammill et al. .................. 260/619 A |
| 4,400,555 | 8/1983 | Mendiratta ............................ 568/728 |
| 4,859,803 | 8/1989 | Shaw .................................... 568/727 |
| 5,087,767 | * 2/1992 | Okamoto .............................. 568/727 |

FOREIGN PATENT DOCUMENTS 0 770 590    5/1997    (EP) .

* cited by examiner

*Primary Examiner*—Michael L. Shippen
(74) *Attorney, Agent, or Firm*—Joseph C. Gil; Aron Preis

(57) ABSTRACT

The present invention relates to a process for the production of bis(4-hydroxyaryl)alkanes by an acid-catalyzed reaction between aromatic hydroxy compounds and ketones, in which the temperature, ketone content and water content of a liquid reaction mixture are adjusted by means of a suitably composed gas phase.

13 Claims, No Drawings

METHOD FOR PRODUCING BIS(4-HYDROXYARYL)ALKANES

The present invention relates to a process for the production of bis(4-hydroxyaryl)alkanes by an acid-catalysed reaction between aromatic hydroxy compounds and ketones, in which the temperature, ketone content and water content of a liquid reaction mixture are adjusted by means of a suitably composed gas phase.

It is known to synthesise bis(4-hydroxyaryl)alkanes by an acid-catalysed reaction between aromatic hydroxy compounds and ketones. U.S. Pat. Nos. 3,634,341 and 3,760,006 describe the influence exerted by the water content of the reaction mixture on catalyst efficiency, and a water content of 2–3 wt. % is indicated as the critical limit for the reaction in a fixed-bed reactor. WO 94/19079 and EP-A 770 590 disclose the continuous removal of water formed in the reaction, by passing a dry inert gas, for example nitrogen, through the reactor in countercurrent. It is shown in U.S. Pat. No. 4,400,555 (EP-A 342 758) and EP-A 754 666 that the selectivity of bis(4-hydroxyaryl)alkane formation in a production process having a plurality of reactors connected in series can be increased if the ketone is distributed among the different reactors; it is proposed in WO 94/19079 that for bis(4-hydroxyaryl)alkane production in a (stripper) column the ketone be supplied in gaseous or liquid form by way of a plurality of dispensing points throughout the length of the column. A disadvantage of the latter process is the major capital investment and control engineering involved in thus proportioning the ketone supply over a plurality of reactors or a plurality of supply points of a stripper. The rate of reaction of bis(4-hydroxyaryl)alkane formation is furthermore reduced by proportioning the ketone supply. The lower reaction rate is accepted in order to increase the selectivity.

A method is required in which simultaneously the reaction is not only more selective, but also proceeds at a faster rate, in order thus to maximise the space-time yield.

It has now been found that bis(4-hydroxyaryl)alkanes can be produced at high selectivity and simultaneously at a high space-time yield if the temperature, ketone content and water content of a liquid reaction mixture are adjusted by means of a suitably composed gas phase. The present invention provides a process for the production of bis(4-hydroxyaryl)alkanes by an acid-catalysed reaction between aromatic hydroxy compounds and ketones, in which there are guided through a reactor a liquid phase which contains aromatic hydroxy compound, ketone and optionally water, and a gas phase which contains aromatic hydroxy compound, ketone and optionally water, at concentrations such that in the reactor water passes over from the liquid phase into the gas phase and ketone from the gas phase into the liquid phase.

The gas phase and the liquid phase may be guided through the reactor either in co-current or in countercurrent. Countercurrent is the preferred modus operandi.

Freely selectable, approximately constant concentrations of ketone and water can be adjusted throughout the length of the reactor at simultaneously approximately constant, freely selectable temperatures, as a result of the process according to the invention. According to the invention it is likewise possible to carry out a method in which, instead of conditions being approximately constant, it is possible to select conditions under which the temperature and/or the concentration of aromatic hydroxy compound, ketone and water in the liquid phase are not constant throughout the length of the reactor. Thus, for example, temperature gradients and/or ketone and/or water concentration gradients can be impressed in the liquid phase. The underlying concept of the process according to the invention is the adjustment of the temperature, the ketone content and the water content in the liquid reaction mixture by means of a suitably composed gas phase.

In the process according to the invention the molar ratio of aromatic hydroxy compound to ketone in the liquid phase supplied to the reactor is generally from 3.5:1 to 125:1, preferably 5:1 to 60:1, particularly preferably 10:1 to 30:1. The liquid phase supplied to the reactor may contain small quantities of water. The water content is preferably from 0 to 2 wt. %.

The molar ratio of aromatic hydroxy compound to ketone in the gas phase supplied to the reactor results from the condition that ketone should pass over from the gas phase into the liquid phase in the reactor at the reaction temperature and reaction pressure. In order to adjust approximately constant ketone concentrations in the liquid phase, the ketone concentration in the gas phase entering the reactor should accordingly be selected to be approximately as high as the concentration which would adjust in the gas phase by way of the dispensed-in liquid phase at the reaction temperature and reaction pressure under conditions of thermodynamic equilibrium. If a ketone concentration gradient is to be adjusted in the reactor, the ketone concentration in the gas phase supplied to the reactor should be selected to be higher or lower than the concentration which would adjust under conditions of thermodynamic equilibrium.

The water concentration in the dispensed gas phase results from the water concentration in the dispensed liquid phase, on the same principle. It must be selected such that in the reactor at the reaction temperature and reaction pressure water passes over from the liquid phase into the gas phase. The water concentration in the gas phase should accordingly be selected to be approximately as high as the concentration which would adjust in the gas phase by way of the dispensed liquid phase at the reaction temperature and reaction pressure under conditions of thermodynamic equilibrium, in order to adjust a constant water concentration in the liquid phase. If a water concentration gradient is to be adjusted in the reactor, the water concentration in the gas phase supplied to the reactor should be selected to be higher or lower than the concentration which would adjust under conditions of thermodynamic equilibrium.

As a result of suitable adjustment of the concentrations in the gas phase and the liquid phase in the reactor, water is removed from, and ketone supplied to, the liquid reaction mixture in continuous manner by the gas phase. The consumption of ketone or the arising of water as a result of reaction are consequently balanced by the phase transition between the gas phase and the liquid phase. In this manner the concentrations of ketone and water in the liquid phase and the temperature in the reactor can be held approximately constant, or a concentration gradient or temperature gradient can be impressed.

This operating characteristic is highly advantageous, because a continuous making-up of spent ketone and the simultaneous continuous removal of water from the liquid phase hold the reaction rate high throughout the length of the reactor. The regulatable, optionally approximately constant reaction conditions in the reactor, and the approximately isothermic operating characteristic enable selectivity to be improved simultaneously.

The temperature in the reactor is between the temperature of crystallisation of the reaction mixture and 130° C. It is adjusted by selecting the pressure in the reactor. If the ketone concentration and the water concentration are held constant throughout the length of the reactor, a highly uniform temperature regime can be achieved. The removal and supply of heat take place, by contrast with the process described in WO 94/19079, not as a result of heating an inert gas stream, but far more effectively principally as a result of local evaporation and condensation. By contrast with the prior art process, the temperature can in this way be held approximately constant throughout the reaction zone.

The pressure to be adjusted for the desired temperature and the desired ketone and water concentrations can be calculated by way of the thermodynamic equilibrium; under operating characteristics without inert gas, it is generally from 5 to 1000 mbar, preferably 15 to 200 mbar. In order to adjust the temperature in the reactor by pre-setting the pressure, an inert gas such as nitrogen can optionally be added to the gas feed.

If a temperature gradient is to be adjusted in the reactor, for example in order to avoid crystallisation of the bis(4-hydroxyaryl)alkane-enriched reaction mixture in the lower part of the reactor, the temperature in the reactor, and even—by way of the ketone concentration and the water concentration in the liquid phase—the temperature of crystallisation of the reaction mixture, can be influenced by generating pressure stages in the reactor or by impressing a concentration gradient.

The temperature of the supplied liquid phase should correspond to, but may also be lower than, the boiling point at the pre-set pressure in the reactor, and the temperature of the supplied gas phase should correspond to, or be slightly higher than, the dew point at the pre-set pressure in the reactor.

When carrying out the process according to the invention, temperature and concentration profiles and/or temperature and concentration stages can naturally be carried out in targeted manner as a result of additional gas and fluid feed dispensing points or as a result of measures which bring about local pressure changes in the reactor.

Suitable acid catalysts for the production of bis(4-hydroxyaryl)alkanes are known to those skilled in the art. They may be homogeneous catalysts, for example, hydrochloric acid, sulfuric acid, boron trifluoride, and the like. Homogeneous catalysts may be dispensed by way of a separate dispensing means and/or together with the liquid phase. Heterogeneous catalysts are preferably used. Catalysts known to those skilled in the art are used as heterogeneous catalysts, for example acid ion exchange resins, solid inorganic acids, functionalised solid inorganic acids, and the like. Catalysts having sulfonic acid groups in an organic, inorganic or combined organic/inorganic matrix are preferably used. The heterogeneous catalysts are preferably used together with sulfur-containing co-catalysts. Such co-catalysts are known to those skilled in the art. They may be dispensed in gaseous form, optionally together with the educt gas stream (for example in the case of $H_2S$) or in homogeneous form together with the liquid phase, or they may be previously fixed on a heterogeneous catalyst. Examples of such catalysts are to be found in U.S. Pat. Nos. 2,468,982, 2,623,908, 2,775,620, 3,634,341, 3,760,006, DE-OS 36 19 450 and DE-OS 37 27 641.

The reactors which may be used are those known to those skilled in the art, which enable an intensive mass transfer to take place between the gas phase and the liquid phase, and simultaneously an intensive contact of the liquid phase with a heterogeneous catalyst. Examples of the latter are multi-phase reactors having a suspended catalyst (gas-stirred tank reactors, bubble columns, three-phase fluidised bed reactors, and the like), multi-phase reactors having a catalyst arranged in fixed manner (for example trickling bed reactors) or rectification columns of various designs. The use of a reactive rectification column is preferred. It is embodied in a manner known to those skilled in the art as a plate column or a packed column. In the preferred embodiment of the process having a heterogeneous catalyst, the latter is introduced into the plate column or a column having ordered or random packing, in a manner known to those skilled in the art. Examples are described in EP-A 670 178; EP-A 461 855; U.S. Pat. Nos. 5,026,459; 4,536,373; WO 94/08681; WO 94/08682; WO 94/08679; EP-A 470 655; WO 97/26971; U.S. Pat. No. 5,308,451; EP-A 755 706; EP-A 781 829, EP-A 428 265; EP-A 448 884; EP-A 640 385; EP-A 631 813; WO 90/02603; WO 97/24174; EP-A 665 041, EP-A 458 472; EP-A 476 938, German utility model 298 07 007.3.

Alternatively, the catalyst can be introduced into external, optionally temperature-controlled reactors, wherein the liquid phase is passed from the column into the reactor and thence to the mass transfer back into the column. The temperatures in the column and the external reactors can be de-coupled by temperature-controlling the streams between the column and the external reactors.

In a preferred embodiment of the process, in which a reactive rectification column is used as the reactor, ketone, aromatic hydroxy compound and optionally water in the desired ratio are dispensed in liquid form in the upper part of the column above the reaction zone. Simultaneous feeding of a suitably composed gas feed in the lower region of the column, below the reaction zone, achieves the continuous transportation, by way of the gas phase, of the water which arises as a result of reaction in the liquid phase, and the subsequent continuous delivery, into the liquid phase, of ketone consumed by the reaction. As a matter of choice, an approximately constant ketone concentration and water concentration or, for example in order to avoid crystallisation of the reaction mixture in the lower part of the reactive rectification column, a temperature gradient and/or a ketone concentration and/or water concentration gradient can be adjusted in the reactor. In the reactive rectification, concentration and/or temperature profiles can be adjusted as a result of the composition of the liquid phase and an optionally deliberately impressed pressure loss and/or as a result of additional dispensing points for gas and/or liquid. If the ketone concentration in the lower part of the column where a higher bis(4-hydroxyaryl)alkane content is present is increased, the reaction mixture has a lower crystallisation point, such that a lower reaction temperature may be selected.

Heat can be supplied to the reactor or removed therefrom by way of optionally installed heat exchangers. The operating characteristic having no heat exchangers is simpler. The mass transfer between the gas phase and the liquid phase within the reactor is optimised in a manner known to those skilled in the art. If, as preferred, the process is carried out as a reactive rectification, the installed separation efficiency is selected dependent on the progress of the reaction, such that the consumed ketone is brought afterwards sufficiently rapidly from the gas phase into the liquid phase, and the water which arises is transported sufficiently rapidly from the liquid phase into the gas phase. Packings or plates known to those skilled in the art are preferably used in addition. If a heterogeneous catalyst is used, it is arranged on the plates or in the packing in a manner known to those skilled in the art. If a homogeneous catalyst and/or a co-catalyst is used, it can be dispensed into the reactor with the liquid dispensing means and/or by way of additional dispensing points. If a co-catalyst in gaseous form is used, it can be brought into the reactor with the gas dispensing means and/or by way of additional dispensing points.

A distillation zone and an evaporator may be situated below the reaction zone. As a result, ketone, water and some of the aromatic hydroxy compound and optionally co-catalyst can be evaporated from the liquid discharge, such that only some of the gas stream must be supplied in external manner. The product stream leaving the latter distillation zone has reduced concentrations of ketone and water and an increased concentration of bis(4-hydroxyaryl) alkane.

The product stream can be worked up in a manner known to those skilled in the art. Thus the bis(4-hydroxyaryl)alkane can be isolated from the product stream, for example by crystallisation (see, for example, DE-OS 42 13 872, EP-A 671 377 or U.S. Pat. No. 5,545,764), extraction with an organic solvent, distillation (see, for example, U.S. Pat. No. 5,785,823) or a combination of the latter measures.

The gas stream which is discharged from the reaction zone at the top is broken down into its components or mixtures of components by mass transfer methods which are known in principle, optionally in conjunction with complete or partial compression. The sub streams thus obtained can then be returned to the process in liquid or gaseous form, wherein the reaction water which has formed is, however, transferred out of the process. The methods known to those skilled in the art can be used for mass transfer, for example partial condensation, distillation, extraction, membrane processes and the like. Following compression, gaseous sub streams can be returned directly to the column in gaseous form without further working-up.

The ratio of the dispensed quantities of liquid phase and gas phase will depend, in a manner known to those skilled in the art, on the reactor type chosen. For example, the latter ratio in reactive rectification, taking account of the hydrodynamic limits resulting from the installed means, is selected such as to ensure an effective mass transfer, and to exclude uneven distribution in the reactor and in addition flooding due to high reactor loading or spray-through due to low reactor loading.

The choice of the quantitative ratio of gas stream to liquid stream also influences the extent to which the reaction conditions can be held constant in the reactor. The composition of the gas stream changes as it flows through the reactor, because ketone is donated to the liquid phase and water is accepted from the liquid phase. As a result, there takes place a slight deviation from the desired constant reaction conditions. The higher the quantitative ratio of gas stream to liquid stream, the smaller the deviation; however, as the quantity of gas increases, so there is a simultaneous increase in the cost of recycling the gas stream. Ratios of gas stream to liquid stream of from 0.01 to 10, in particular 0.05 to 2, have proved favourable.

The liquid stream supplied to the reactor is composed of educts which are supplied fresh to the process and/or are circulated, and optionally the recycled flow from a partial condensation of the gas stream. The gas stream supplied to the reactor is composed of components which are supplied fresh to the process and/or circulated, and optionally a component which is obtained as a result of partial evaporation of the liquid stream. A distillation part can be installed between the evaporator and the reaction part, which serves to improve recycling of the higher-boiling components.

Suitable aromatic hydroxy compounds for the process according to the invention are not substituted in the p position and contain no second-order substituents such as cyano, carboxy or nitro groups; examples which might be named are phenol, o-cresol and m-cresol, 2,6-dimethylphenol, o-tert-butylphenol, 2-methyl-6-tert-butylphenol, o-cyclohexylphenol, o-phenylphenol, o-isopropylphenol, 2-methyl-6-cyclopentylphenol, o-chlorophenol and m-chlorophenol, 2,3,6-trimethylphenol. Phenol, o-cresol and m-cresol, 2,6-dimethylphenol, o-tert-butylphenol and o-phenylphenol are preferred; phenol is particularly preferred.

Ketones having aliphatic, araliphatic or aromatic groups on the carbonyl function can be used in the process according to the invention; for example including ω-phenylacetophenone or benzophenone.

Ketones which contain at least one aliphatic group on the carbonyl function are preferably used; examples which might be named are acetone, methyl ethyl ketone, methyl propyl ketone, methyl isopropyl ketone, diethyl ketone, acetophenone, cyclohexanone, cyclopentanone, methyl-, dimethyl- and trimethyl cyclohexanone, which may also have germinal methyl groups such as 3,3-dimethyl-5-methyl cyclohexanone (hydroisophorone). Acetone, acetophenone, cyclohexanone and homologues thereof carrying methyl groups are preferred; acetone is particularly preferred.

Suitable educts for the process according to the invention are also the mother liquors which remain following extraction of the bis(4-hydroxyaryl)alkanes, which are recycled into the process after the dosing of the spent hydroxy compounds and optionally removal of a certain proportion in order to avoid undesirable by-product enrichment; in the case of bisphenol A synthesis, such mother liquors contain approximately 75 to 90 wt. % phenol and 10 to 25 wt. % by-products, having the following composition:

| | |
|---|---|
| Bisphenol A | 25–80 wt. % |
| o,p-bisphenol | 5–20 wt. % |
| Trisphenol | 2–10 wt. % |
| Chroman | 2–20 wt. % |
| 1,3,3-trimethyldihydroxy phenylindane | 1–15 wt. % |
| Other by-products | 0.5–10 wt. % |

In the process according to the invention, in particular when carried out in a reaction rectification column, higher reaction rates and hence higher space-time yields are obtained as a result of the continuous and efficient extraction of the reaction water which can inhibit the reaction by blocking the catalyst surface, and the continuous making-up of the ketone. At the same time, a highly constant temperature regime is possible, because exothermic or endothermic effects which occur in the system do not lead to a temperature change, but are compensated by partial evaporation or condensation. Owing to the shorter residence time in the reactor and the regulation of the temperature, water content and ketone content of the liquid phase in the reactor, increased reaction selectivity and hence reduced by-product formation, and increased product quality are observed. The latter are also conditions which improve catalyst life.

A combination of the process according to the invention with classic reaction technique is naturally also conceivable for the preparation of bis(4-hydroxyaryl)alkanes. Thus, for example, a classic fixed-bed reactor in which the initial reaction of the ketone is carried out may be inserted upstream of the process according to the invention, in which the remaining reaction is carried out until completion of the reaction. The initial reaction in the fixed-bed reactor at a high ketone concentration, low water concentration and low starting temperature leads to a high space-time yield and good product quality in the crude product which is dispensed as the liquid phase into the process according to the invention. In this case the remaining reaction can be carried out under the advantageous conditions of the process according to the invention such as, for example, an approximately constant low water concentration and/or high ketone concentration and approximately constant temperature.

The advantage of this combination of reaction techniques lies in minimising capital costs.

EXAMPLES

Examples 1 to 7

Acetone and phenol were reacted to bisphenol A in a 30 cm long, 50 mm diameter, countercurrent tube reactor charged with 160 g catalyst. The catalyst was in cylindrical wire mesh packing bodies which left open approximately 60% free volume for the gas stream and enabled an intensive mass transfer to take place. A sulfonated polystyrene resin (K1131, from Bayer AG) which is cross-linked with 2 wt. % divinylbenzene was used as catalyst, modified with 5 mol % 2,2-dimethylthiazolidine.

Examples 1 to 3

The quantitative stream of the gas feed was varied while the educt composition remained constant.

| Composition | Acetone [wt. %] | Water [wt. %] | Phenol [wt. %] |
|---|---|---|---|
| Liquid feed | 4.00 | 0.25 | 95.75 |
| Gas feed | 59.5 | 6.6 | 33.9 |

| Example | 1 | 1a | 2 | 2a | 3 | 3a |
|---|---|---|---|---|---|---|
| Head temperature [° C.] | 60.3 | 60.2 | 60.2 | 60.1 | 57.5 | 58.5 |
| Base temperature [° C.] | 63.1 | 62.9 | 63.1 | 63.0 | 63.3 | 63.1 |
| Pressure [mbar] | 30 | 30 | 30 | 30 | 30 | 30 |
| Feed-head [g/h] | 600 | 600 | 600 | 600 | 600 | 600 |
| Feed-base [g/h] | 600 | 600 | 300 | 300 | 150 | 150 |
| Bottom [g/h] | 690 | 688 | 640 | 650 | 651 | 649 |
| Distillate [g/h] | 485 | 495 | 250 | 240 | 102 | 100 |

The composition of the crude product below the reaction zone in the latter countercurrent tube reactor is shown in the Table which follows. It must be noted here that in this simple laboratory apparatus no extraction by distillation of the high-boiling fractions acetone and water takes place below the reaction zone, such that the latter appear with the bottom product. In the analyses which follow, therefore, the sum of all the bottom products (including acetone and water) is 100%.

| | 1 | 1a | 2 | 2a | 3 | 3a |
|---|---|---|---|---|---|---|
| Bottom product analysis | | | | | | |
| Phenol [wt. %] | 78.9 | 78.8 | 77.0 | 79.2 | 78.9 | 78.2 |
| Dimethylxanthene [wt. %] | 0.08 | 0.09 | 0.08 | 0.08 | 0.06 | 0.06 |
| o,o'-BPA [wt. %] | 0.013 | 0.014 | 0.015 | 0.014 | 0.013 | 0.013 |
| o,p'-BPA [wt. %] | 0.42 | 0.44 | 0.49 | 0.47 | 0.51 | 0.54 |
| p,p'-BPA [wt. %] | 13.3 | 13.5 | 15.5 | 14.9 | 15.1 | 15.6 |
| Chroman [wt. %] | 0.031 | 0.035 | 0.033 | 0.033 | 0.029 | 0.030 |
| BPA-indane [wt. %] | 0.004 | 0.004 | 0.004 | 0.004 | 0.005 | 0.008 |
| Spiroindane [wt. %] | 0.021 | 0.023 | 0.022 | 0.021 | 0.020 | 0.020 |
| Trisphenol [wt. %] | 0.15 | 0.17 | 0.15 | 0.15 | 0.15 | 0.16 |
| Mol 402 [wt. %] | 0.001 | 0.001 | 0.007 | 0.006 | 0.001 | 0.001 |

-continued

| | 1 | 1a | 2 | 2a | 3 | 3a |
|---|---|---|---|---|---|---|
| Σ unknown composition [wt. %] | 0.016 | 0.019 | 0.080 | 0.040 | 0.040 | 0.050 |
| Acetone [wt. %] | 6.7 | 6.6 | 6.3 | 5.0 | 4.9 | 5.0 |
| Water [wt. %] | 0.36 | 0.31 | 0.29 | 0.08 | 0.27 | 0.33 |
| Example | | | | | | |
| Selectivity for p,p'-BPA [%] | 94.8 | 94.4 | 94.6 | 94.7 | 94.8 | 94.7 |
| Space-time yield [g (BPA)/ml (cat) · h] | 0.43 | 0.43 | 0.46 | 0.45 | 0.46 | 0.47 |
| Space-time yield [g (BPA)/g (cat) · h] | 0.57 | 0.57 | 0.61 | 0.60 | 0.61 | 0.63 |

Examples 4 to 7

The water concentration in the liquid phase and the reaction temperature were varied

| | 4 | | 5 | | 6 | | 7 | |
|---|---|---|---|---|---|---|---|---|
| | Li-quid feed | Gas feed | Li-quid feed | Gas feed | Liquid feed | Gas feed | Liquid feed | Gas feed |
| Example | | | | | | | | |
| Acetone [wt. %] | 4.0 | 57.8 | 4.0 | 59.5 | 4.0 | 60.30 | 4.0 | 60.8 |
| Water [wt. %] | 0.50 | 12.5 | 0.25 | 6.6 | 0.10 | 2.7 | 0.00 | 0.00 |
| Phenol [wt. %] | 95.50 | 29.7 | 95.75 | 33.9 | 95.90 | 36.9 | 96.00 | 39.2 |

| Example | 4 | 4a | 5 | 5a | 6 | 7 |
|---|---|---|---|---|---|---|
| Head temperature | 56.2 | 56.2 | 60.2 | 60.1 | 63.5 | 65.7 |
| Base temperature [° C.] | 58.8 | 58.7 | 63.1 | 63.0 | 66.1 | 68.5 |
| Pressure [mbar] | 30 | 30 | 30 | 30 | 30 | 30 |
| Feed-head [g/h] | 600 | 600 | 600 | 600 | 600 | 600 |
| Feed-base [g/h] | 300 | 300 | 300 | 300 | 300 | 300 |
| Bottom [g/h] | 660 | 655 | 640 | 650 | 680 | 670 |
| Distillate [g/h] | 235 | 238 | 250 | 240 | 220 | 225 |

The composition of the crude product below the reaction zone in the latter countercurrent tube reactor can be seen from the Table which follows. It must be noted here that in this simple laboratory apparatus there is no extraction by distillation of the high-boiling fractions acetone and water below the reaction zone, such that the latter products appear with the bottom product. In the analyses which follow, therefore, the sum of the bottom products (including acetone and water) is 100%.

| | 4 | 4a | 5 | 5a | 6 | 6a |
|---|---|---|---|---|---|---|
| Bottom product analysis | | | | | | |
| Phenol [wt. %] | 81.6 | 82.0 | 77.0 | 79.2 | 75.5 | 74.4 |
| Dimethylxanthene [wt. %] | 0.05 | 0.05 | 0.08 | 0.08 | 0.09 | 0.09 |
| o,o'-BPA [wt. %] | 0.012 | 0.012 | 0.015 | 0.014 | 0.015 | 0.017 |
| o,p'-BPA [wt. %] | 0.32 | 0.33 | 0.49 | 0.47 | 0.61 | 0.72 |
| p,p'-BPA [wt. %] | 11.7 | 11.5 | 15.5 | 14.9 | 17.2 | 18.8 |
| Chroman [wt. %] | 0.018 | 0.018 | 0.033 | 0.033 | 0.046 | 0.068 |
| BPA-indane [wt. %] | 0.003 | 0.000 | 0.004 | 0.004 | 0.011 | 0.024 |
| Spiroindane [wt. %] | 0.012 | 0.010 | 0.022 | 0.021 | 0.037 | 0.058 |
| Trisphenol [wt. %] | 0.10 | 0.09 | 0.15 | 0.15 | 0.22 | 0.29 |
| Mol 402 [wt. %] | 0.001 | 0.001 | 0.007 | 0.006 | 0.007 | 0.009 |

-continued

|  | 4 | 4a | 5 | 5a | 6 | 6a |
|---|---|---|---|---|---|---|
| Σ unknown composition [wt. %] | 0.02 | 0.02 | 0.08 | 0.04 | 0.04 | 0.05 |
| Acetone [wt. %] | 5.6 | 5.5 | 6.3 | 5.0 | 5.9 | 5.3 |
| Water [wt. %] | 0.50 | 0.50 | 0.29 | 0.08 | 0.25 | 0.16 |
| Example |  |  |  |  |  |  |
| Selectivity for p,p'-BPA [%] | 95.6 | 95.6 | 94.6 | 94.7 | 94.2 | 93.4 |
| Space-time yield [g (BPA)/ml (cat) · h] | 0.36 | 0.35 | 0.46 | 0.45 | 0.55 | 0.59 |
| Space-time yield [g (BPA)/g (cat) · h] | 0.48 | 0.47 | 0.61 | 0.60 | 0.73 | 0.79 |

Examples 8 to 10

The experimental apparatus and method correspond to those of experimental Examples 1–7. Different catalysts were used in this series. All the catalysts were modified with 5 mol % 2,2-dimethylthiazolidine.

The composition of the educt streams was constant in this series of Examples:

| Composition | Acetone [wt. %] | Water [wt. %] | Phenol [wt. %] |
|---|---|---|---|
| Liquid feed | 4.00 | 0.5 | 95.5 |
| Gas feed | 57.8 | 12.5 | 29.7 |

| Example | 8 | 9 | 10 |
|---|---|---|---|
| Head temperature [° C.] | 56.2 | 56.2 | 56.2 |
| Base temperature [° C.] | 58.8 | 58.8 | 58.8 |
| Pressure [mbar] | 30 | 30 | 30 |
| Feed-head [g/h] | 600 | 540 | 600 |
| Feed-base [g/h] | 300 | 270 | 300 |
| Bottom [g/h] | 685 | 620 | 700 |
| Distillate [g/h] | 215 | 180 | 200 |
| Catalyst | Lewatit K 1221 Bayer | Amberlyst A 31 Röhm & Haas | Lewatit K 1431 Bayer |
| Catalyst used (g) | 200 | 180 | 200 |

The composition of the crude product below the reaction zone in the latter countercurrent tube reactor can be seen from the Table which follows. It must be noted here that in this simple laboratory apparatus there is no extraction by distillation of the high-boiling fractions acetone and water below the reaction zone, such that the latter products appear with the bottom product. In the analyses which follow, therefore, the sum of all the bottom products (including acetone and water) is 100%.

| Bottom product analysis | 8 | 9 | 10 |
|---|---|---|---|
| Phenol [wt. %] | 80.0 | 85.0 | 87.1 |
| Dimethylxanthene [wt. %] | 0.00 | 0.05 | 0.00 |
| o,o'-BPA [wt. %] | 0.013 | 0.010 | 0.006 |
| o,p'-LBPA [wt. %] | 0.53 | 0.37 | 0.21 |
| p,p'-DPA [wt. %] | 12.3 | 9.6 | 7.1 |
| Chroman [wt. %] | 0.044 | 0.027 | 0.020 |
| BPA-indane [wt. %] | 0.006 | 0.004 | 0.008 |
| Spiroindane [wt. %] | 0.014 | 0.013 | 0.023 |
| Trisphenol [wt. %] | 0.051 | 0.063 | 0.045 |
| Mol 402 [wt. %] | 0.007 | 0.005 | 0.000 |
| Σ unknown composition [wt. %] | 0.047 | 0.033 | 0.039 |
| Acetone [wt. %] | 6.3 | 4.3 | 4.8 |
| Water [wt. %] | 0.55 | 0.54 | 0.61 |

| Example | 8 | 9 | 10 |
|---|---|---|---|
| Selectivity for p, p'-BPA [%] | 94.0 | 94.4 | 94.7 |
| Space-time yield [g (BPA)/g (cat) h] | 0.42 | 0.33 | 0.25 |

What is claimed is:

1. A process for the production of bis(4-hydroxyaryl) alkanes by an acid-catalysed reaction between aromatic hydroxy compounds and ketones, in which there are guided through a reactor a liquid phase which contains an aromatic hydroxy compound, ketone and optionally water, and a gas phase which contains an aromatic hydroxy compound, ketone and optionally water, at concentrations such that in the reactor water passes over from the liquid phase into the gas phase and ketone from the gas phase into the liquid phase.

2. A process according to claim 1, in which the gas phase and the liquid phase are guided through the reactor in countercurrent.

3. A process according to claim 1, in which the concentrations of aromatic hydroxy compound, ketone and optionally water in the gas phase supplied to the reactor correspond to those present in a gas phase which, under the conditions of temperature and pressure prevailing in the reactor, is in thermodynamic equilibrium with the liquid phase supplied to the reactor.

4. A process according to claim 1, in which the concentrations of aromatic hydroxy compound, ketone and optionally water in the gas phase supplied to the reactor and the liquid phase supplied to the reactor are selected such that the temperature and/or the concentrations of aromatic hydroxy compound, ketone and water in the liquid phase are not constant throughout the length of the reactor.

5. A process according to claim 1, in which the reactor contains a heterogeneous acid catalyst.

6. A process according to claim 5, in which an acid ion exchange resin is used as the catalyst.

7. A process according to claim 1, in which the catalyst is used together with sulfur-containing co-catalysts.

8. A process according to claim 1, in which the temperature in the reactor is higher than the temperature of crystallisation of the reaction mixture and is a maximum of 130° C.

9. A process according to claim 1, in which the pressure in the reactor is from 5 mbar to 1000 mbar.

10. A process according to claim 1, in which the aromatic hydroxy compound is phenol.

11. A process according to claim 1, in which the ketone is acetone.

12. A process according to claim 1, in which a reactive rectification column is used as the reactor.

13. A process according to claim 1, in which the liquid phase supplied to the reactor contains aromatic hydroxy compound, ketone and reaction products formed therefrom.

* * * * *